United States Patent [19]

Canata et al.

[11] 3,968,017

[45] July 6, 1976

[54] PROCESS AND AN EQUIPMENT FOR PRODUCING CRYSTALLINE CITRIC ACID FROM SOLUTIONS OF ALKALINE CITRATES

[75] Inventors: Pierluigi Canata, Pellaro (Reggio Calabria); Giampiero Longobardi, Rome, both of Italy

[73] Assignees: Compagnia Tecnica Industrie Petroli S.p.A., Rome; Liquichimica S.p.A., Milan, both of Italy

[22] Filed: Feb. 6, 1975

[21] Appl. No.: 547,556

[30] Foreign Application Priority Data
Feb. 13, 1974 Italy .................................. 48311/74

[52] U.S. Cl. ............................ 204/180 P; 204/131; 204/301
[51] Int. Cl.² ......................................... B01D 13/02
[58] Field of Search ................. 204/98, 180 P, 301, 204/131

[56] References Cited
UNITED STATES PATENTS

| | | |
|---|---|---|
| 2,777,811 | 1/1957 | McRae et al. ...................... 204/151 |
| 3,003,940 | 10/1961 | Mason et al. ...................... 204/180 P |
| 3,086,928 | 4/1963 | Schulz ................................. 204/72 |
| 3,411,998 | 11/1968 | Wallman et al. ............. 204/180 P X |

*Primary Examiner*—John H. Mack
*Assistant Examiner*—A. C. Prescott
*Attorney, Agent, or Firm*—Olson, Trexler, Wolters, Bushnell & Fosse, Ltd.

[57] ABSTRACT

A process for producing citric acid in crystalline form from solutions of alkaline citrates, comprising sequentially the stages of:
 a. partially converting by electrodialysis the alkaline citrate to citric acid;
 b. concentrating by hot fractional crystallization the solution of citric acid and alkaline citrate as obtained in (a);
 c. separating by centrifugation the crystalline citric acid from the concentrated solution coming from (b);
 d. re-cycling the mother liquors of crystallization residual from the separating operation (c) part to the electrodialysis stage (a) and part to the stage of crystallization (b).

5 Claims, 4 Drawing Figures

PROCESS AND AN EQUIPMENT FOR PRODUCING CRYSTALLINE CITRIC ACID FROM SOLUTIONS OF ALKALINE CITRATES

The present invention relates to a process and to the equipment for producing crystalline citric acid from solutions of alkaline citrates. More particularly this invention relates to a process for producing crystalline citric acid starting from solutions of the most general type of alkaline citrates, utilizing electrodialysis cells, with cationic semipermeable membranes.

It is known from the prior art, that the citric acid is industrially produced either by mycologic fermentation (citromycetes, *Aspergillus niger*, etc.) of solutions of carbohydrates, molasses, etc., or from the fruit juices (citrus, pineapples, etc.) by action of $H_2SO_4$ on the juice neutralized by milk of calcium (calcium citrate) and subsequent purifying by chemical or physical way.

It is to be noted, however, that both said techniques are not free from drawbacks, due both to the difficulties inherent to the purifying operations by chemical way and to the limitation to the sole calcium citrate solution.

Recently certain methods have been proposed for producing citric acid having recourse to electrodialytic techniques in cells with semipermeable membranes. Also in this case, however, it is to be remarked that by the cells used up to day, including both anionic and cationic membranes, the obtained results are not entirely satisfactory in view of the scarce resistance against wear offered by the anionic membranes, and by the non adequate geometry of the liquid circuits inside the cells, as it will be set out later on, with greater details.

Accordingly, a main purpose of this invention is that of providing a process wherein, by having recourse to an improved type of electrodialytic cells both the drawbacks of the two above referred conventional techniques, and those concerned with the present or conventional cells will be overcome.

Another purpose of this invention is that of embodying a process for the production of citric acid allowing both the fermentation solutions containing alkaline citrates, and the solutions of alkaline citrates having a different origin, to be utilized with no other intermediate operation.

A particular advantage of this invention resides in that it provides a process which appears to be exceptionally suitable for treatment of the liquors, rich of alkaline citrates, obtained by fermentation of n-paraffins, by means of the *Candida lipolytica* yeast.

A further advantage consists in the possibility, offered by the process according to this invention, of obtaining at parity of conversion degree of the citrate to citric acid, a higher efficiency.

Said advantages, and particularly the last cited one, which affords relevant economies in the costs of production, are the consequence of both the particular types of electrolytic cells as proposed by this invention, and the combined use of at least two of them, different as structure and number of cells, and of the operative modes of this process. In fact, differently from the cells as previously used for this purpose (see the U.S. Pat. No. 3,086,928 of Apr. 23, 1963) the cells according to the present invention have a different subdivision into compartments, a different arrangement of the hydraulic circuits and are embodied using only semipermeable membranes of the cationic type.

As it has been experimentally tested, these cells show, with respect to the preceding cells, a higher power efficiency, at parity of obtained degree of conversion. This fact can also appear to be intuitive if attention will be paid to the possibility of utilizing cells with three compartments, which have obviously a minor electric resistance for the most of the conversion and of utilizing cells with four compartments for reaching a higher conversion degree, this system being adopted in a preferred embodiment of the invention as described hereinafter.

The fact that these cells consist of sole cationic membranes, besides simplifying under the practical standpoint the maintenance and the stock of the reserve materials, has the remarkable advantage of offering a longer duration of the useful life, as at the present status of the techniques of manufacture of the membranes, the cationic membranes result to have an average duration far longer than that of the corresponding anionic membranes.

The cationic membranes used in the cells are made by IONICS Incorporated. The types as follows have been used: Cationic membranes made according to the U.S. Pat. No. 2,731,411, of Jan. 17, 1956, assigned to M. T. Clarke (Type CR61) and to the U.S. Pat. No. 3,657,104 of Apr. 18, 1972 assigned to R. B. Hogdon (type CR61-70).

Various degrees of conversion can be obtained from the electrodialysis cells. It has been experimentally tested that the power unitary consumption for converting the citrate to citric acid increases to a remarkable extent when the obtained degree of conversion increases, and becomes very high for the global conversion of the starting citrate.

In order to obviate this inconvenience, according to this invention, a technological operation of fractional crystallization of citric acid from mother liquors containing non-converted citrate as impurity, has been introduced and perfected. It has been experimentally tested that within a broad field of concentration of the citrate within the mother liquors of crystallization of the citric acid, it is possible to obtain by fractional crystallization, the pure citric acid. Depending upon the conditions of temperature and pressure within the crystallizer, it is possible to obtain by this way, citric acid having a high purity degree both in its anhydrous form and in the mono-hydrate form.

When the concentration of the citrate in the mother liquors increases the crystallization conditions become worse, mainly due to the remarkable increase of the viscosity of the mother liquors.

In order to avoid the non-converted citrate from accumulating in the crystallization mother liquors, and the consequent worsening of the crystallization conditions, one part of the mother liquors is re-cycled, according to the process of this invention, to the electrodialysis cell.

Experimentally have been determined the optimum conditions of individual operation of the variability field of the two parameters which define the conditions of the system: degree of conversion in the electrodialytic cells and concentration of the citrate in the crystallization mother liquors.

The optimum fields of variability appeared to be as follows:

degree of conversion 90% to 99.9%
Concentration of the citrate 0% to 10% by weight as equiv- -continued alent tri-hydrogen citrate.

Moreover, and this is a further advantage offered by this invention, a recovery of the heat developed in the electrodialytic cells is provided, in order to utilize said heat for heating the crystallizer. In fact most of the electric power used in the electrodialytic cells for performing the conversion will be dissipated in form of heat. The cells require therefore an important cooling circuit in order to maintain the temperature at the optimum operating conditions which are from 50°C to 90°C. Parallel, the crystallization of the citric acid requires a remarkable amount of heat for vaporizing the water and reaching the concentration of crystallization. According to the operating conditions, the temperature of the crystallizer can vary from 20°C to 60°C.

The heat exchange between the electrodialytic cells and the crystallizer has been embodied by means of a circuit of the cathodic solution of the alkaline base. As it will be more clearly said later on, the hot cathodic solution outflowing from the cells is collected in a container wherefrom it will be taken by a pump in order to be sent to the heat exchanger for heating the crystallizer. The cooling of the cathodic solution is completed in another heat exchanger by the normal circuit of cooling water.

As far as the process according to this invention is concerned, it consists generally, in a partial conversion of the alkaline citrate into acid by the technique of the electrodialysis followed by a fractional crystallization in order to obtain crystalline citric acid from the mother liquors of crystallization containing citric acid and non-converted alkaline citrate. One fraction of the crystallization mother liquors will be recycled to the electrodialytic conversion cells in order to avoid the non-converted citrate from accumulating in the crystallizer. Depending upon the conditions of temperature and of pressure maintained in the crystallizer it will be possible to obtain either anhydrous citric acid or monohydrate acid.

The electrodialytic conversion cells used in this process have been expressly studied in order to obtain a high degree of conversion with a low power consumption; they can have either three or four compartments.

Depending upon the alkaline citrate to be converted, (mono-hydrogen, bi-hydrogen or tri-hydrogen) and according to the degree of conversion to be obtained, cells with three compartments or cells with four compartments will be used, or more frequently, as aforesaid, a suitable combination of these cells.

Therefore, a specific object of this invention is a process for producing citric acid in crystalline form, from solutions of alkaline citrates, characterized in comprising sequentially the operations of:

a. partially converting by electrodialysis the alkaline citrate to citric acid;
b. concentrating by hot fractional crystallization under vacuum, the solution of citric acid and alkaline citrate obtained as per (a);
c. separating by centrifugation the crystalline citric acid from the concentrated solution obtained in stage (b);
d. re-cycling the crystallization mother liquors residual from the centrifugation operation (c), partly to the electrolytic conversion stage (a) and partly to the fractional crystallization (b), the heat necessary to crystallization (c) being supplied by heat exchange by the hot cathodic solution of the electrodialysis stage (a).

Preferably, as aforesaid, the electrodialysis will be carried out at temperatures between 50°C and 90°C, and the crystallization of the citric acid at 20°–60°C.

As far as the recycling operation (d) of the mother liquors of crystallization is concerned, the preferable results have been obtained by a re-cycle of 10% by weight to the electrodialysis stage, while the remainder (90% by weight) is re-cycled to the crystallization stage.

This invention indicates also the structural equipments to be adopted in the manufacture of the electrodialysis cells suitable for the cited process. An essential feature of these cells is that of having only cationic selectively permeable membranes. Said cells comprise at least two cationic semipermeable membranes which define an internal compartment, or internal compartments for the feed solution between the anolytic and the catolytic zones of the cell.

In the embodiment providing only two semipermeable membranes, (cell with three compartments), the feed of the central compartment is obtained by a solution of alkaline citrate; in the three membrane form (cell with four compartments) the citrate is fed to one of the two central compartments (the cathodic compartment) while in the second central compartment (anodic compartment) will be sent the solution of citrate plus citric acid obtained by electrodialysis in the cathodic central compartment.

Preferably, when a high degree of conversion is to be obtained, use is made of a three compartment cell and a four compartment cell, arranged in series, with recycle of the crystallization mother liquors to the central anodic compartment of the second four compartment cell.

The present invention will be now described with particular reference to the attached drawings showing preferred embodiments of the invention itself.

Figure 1:
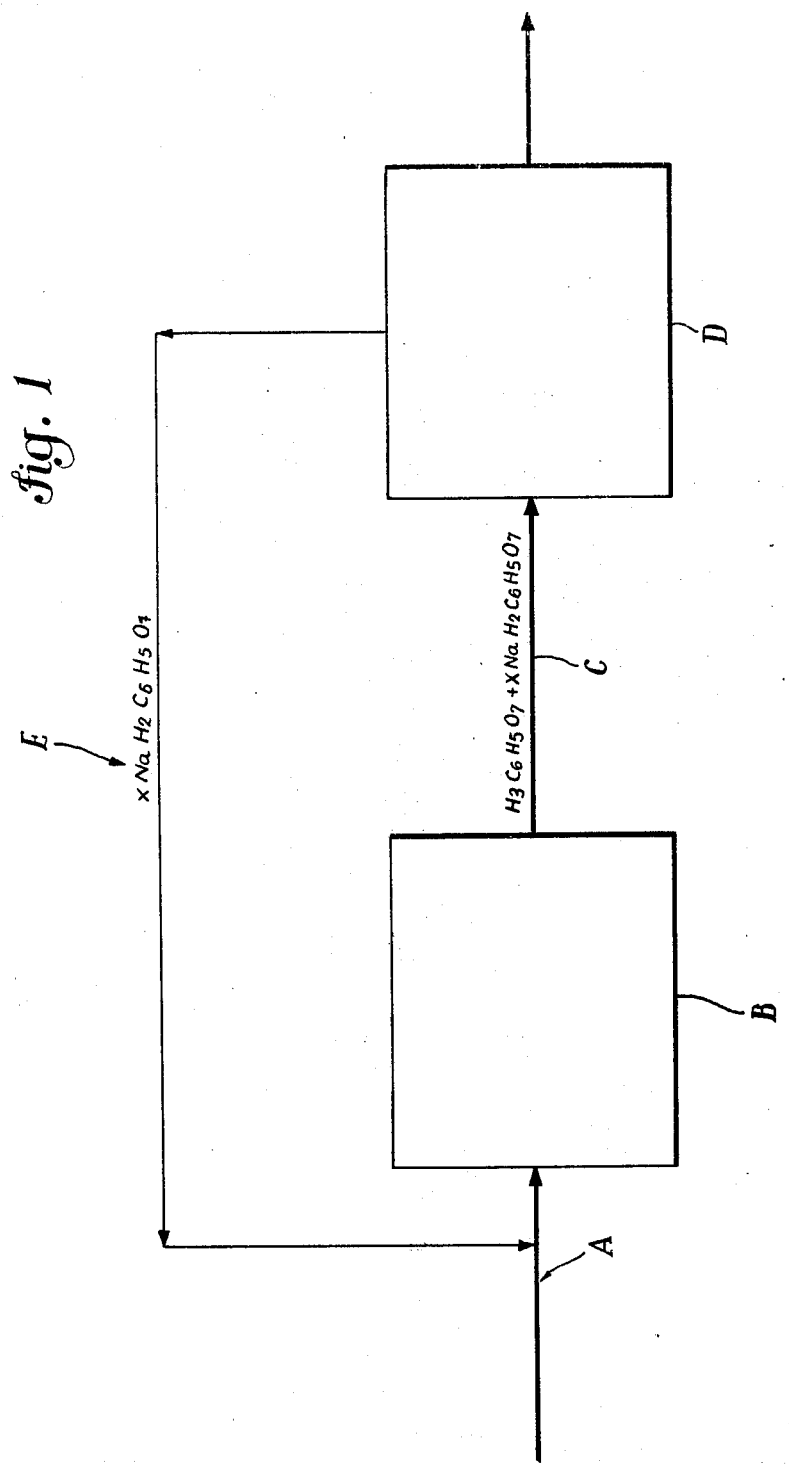
FIG. 1 is a block diagram showing, in their sequence, the basic operations of the process according to this invention.

With particular reference to the drawings: in FIG. 1 the general diagram of the process according to this invention has been shown, wherein a feed solution (A) of monosodium citrate is submitted in (B) to electrodialysis; the resulting solution of monosodium citrate and citric acid (C) is submitted to crystallization in (D) with recycle (E) of part of the crystallization mother liquors still containing citrate to the electrodialysis stage (B).

Figure 2:
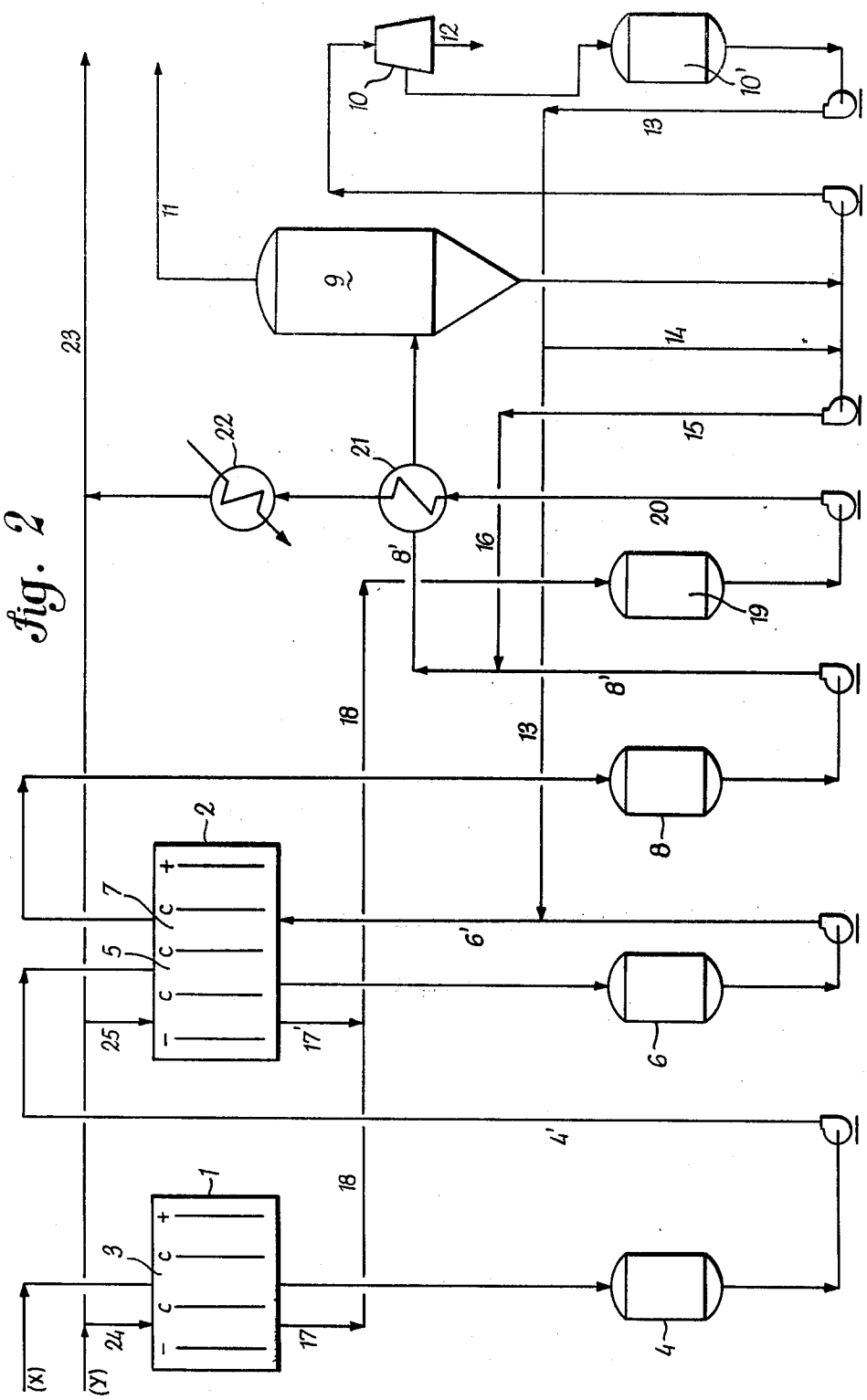
FIG. 2 is a diagram of a plant for embodying the process of FIG. 1.

FIG. 2 shows a preferred industrial embodiment of the process according to this invention. The plant provides one electrodialysis cell 1 with three compartments and one electrodialysis cell 2, with four compartments, arranged in series. In the first cell 1, fed with a solution of alkaline citrate X into the central compartment 3 by electrodialysis a solution of citric acid and alkaline citrate is obtained, and said solution is collected in 4 and pumped through 4' to the cathodic compartment 5 of the cell 2. In this cell a more concentrated solution of citric acid is obtained, and collected in 6 and pumped through 6' to the anodic compartment 7 of said cell 2. Therefrom the solution still more concentrated in citric acid, is collected in 8 and pumped through 8' to the crystallizer 9. Therefrom the crystallization solution is sent to the centrifugal separator 10, while the condensation steam will be discharged through 11. The citric acid separated in 10, is collected in 12, while the residual crystallization mother liquors from 10, collected in 10' are recycled in part through 13 and 6' to the anodic compartment 7 of the four compartment cell 2, and in part through 14, 15, 16 and 8' to the crystallizer 9. Thus an advantageous recycle of the crystallization mother liquors is effected, with a suitable distribution to the crystallizer and to the electrodialysis cells so as to avoid on one side an excessive concentration of citrate in the stream of the mother liquors recycled to the crystallizer and on the other side to reach a higher degree of conversion to citric acid.

As far as the utilization of the heat developed in the electrodialysis cells 1 and 2, as thermal source for the crystallization operation, in 9, the catolytic solutions (water solutions of NaOH) of both cells are sent through 17, 17' and 18 to a collecting container 19 and then, under the action of a pump, through 20, to the heat exchanger 21 where they give most of their heat to the crystallizer 9, and then are further cooled in an exchanger 22 by a common circuit of cooling water. The residual solution of caustic soda is sent to the recovery line 23 where it mixes with the water stream (Y) partially utilized to fed the cathodic compartments of both cells (1) and (2) through 24 and 25.

Figure 3:
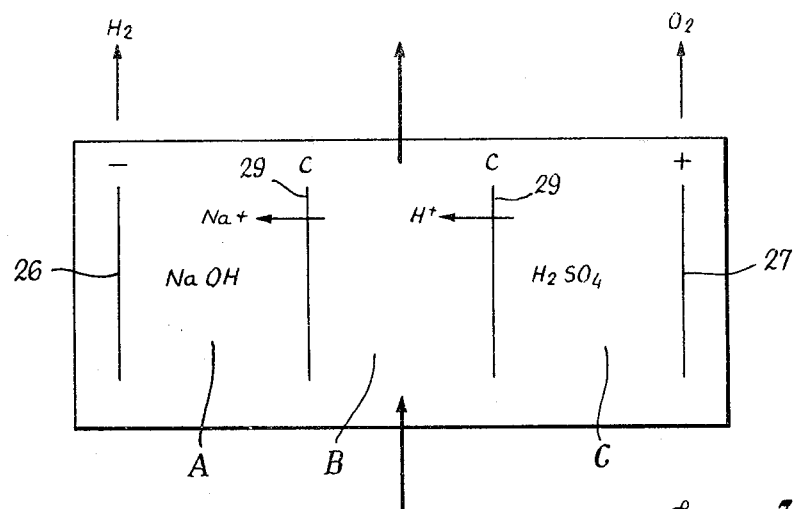
FIG. 3 is a diagrammatic illustration of a three compartment electrodialysis cell according to this invention.

With reference to FIG. 3 of the drawings, in said figure it has been shown a cell 26 with three compartments defined by the two electrodes, the anode 27 and the cathode 28 and by the two cationic membranes 29. The three compartments are the cathodic compartment A, the central compartment B and the anodic compartment C, respectively. In the cathodic compartment A, a 1N to 3N solution of NaOH is maintained. In the central compartment is maintained a solution of partially converted citrate. In the anodic compartment C, a 0.25 N solution of $H_2SO_4$ is maintained.

The citrate is fed to the central compartment B where, due to the passage of the current and to the presence of the cationic semipermeable membranes 29 the conversion is effected, namely the replacement of the ions $Na^+$ which migrate towards the cathodic compartment (A) by the ions $H^+$ which come from the anodic compartment (C).

To the cathodic compartment water is fed, and therefrom a solution of caustic soda is extracted, said solution being formed by the sodium ions migrated from the compartment (B) and the hydroxyl ions freed by the discharge of the ions $H^+$ to the cathode 28 with the consequent hydrogen generation.

At the anodic compartment (C) there is practically no consumption of sulphuric acid as the ions $H^+$ migrating towards the central compartment B are replaced by as many ions $H^+$ produced by the discharge of the oxygen at the anode 27.

Figure 4:
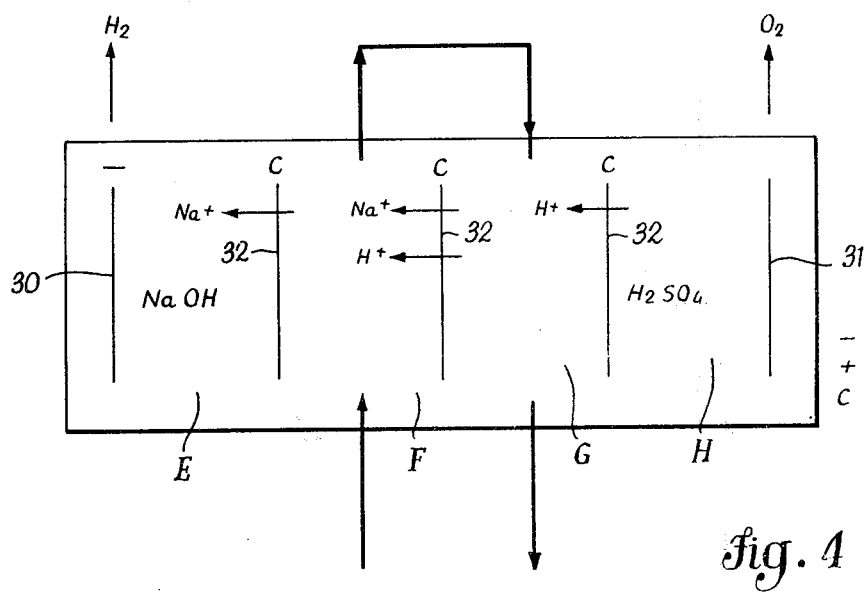
FIG. 4 is a diagrammatical illustration of a four compartment electrodialysis cell according to this invention.

FIG. 4 shows an electrodialysis cell with four compartments and precisely:
   E. cathodic compartment
   F. central cathodic compartment
   G. central anodic compartment
   H. anodic compartment
defined by the cathode 30 and the anode 31 and by three semipermeable membranes 32.

In the cathodic compartment (E) and in the anodic compartment (H) the operating conditions are analogous to those of the three compartment cell.

In the central cathodic compartment (F) a solution of citrate, partially converted to citric acid is maintained. In the central anodic compartment (G) a solution at the maximum degree of conversion to citric acid is maintained. The solution of citrate is fed to the cathodic central compartment (F) wherefrom it is extracted, partially converted for being sent to the central anodic compartment (G) where the conversion is completed.

The present invention has been described with particular reference to certain specific embodiments thereof, being however understood that changes and modifications might be entered therein without thereby departing from the scope of the present industrial privilege.

Having thus described the present invention, what is claimed is:

1. A process for producing citric acid in crystalline form from solutions of alkaline citrates, characterized in comprising sequentially the stages of:
   a. partially converting by electrodialysis the alkaline citrate to citric acid;
   b. concentrating by hot fractional crystallization the solution of citric acid and alkaline citrate as obtained in (a), heat for the crystallization being supplied by heat exchange from the hot cathodic solution of electrodialysis stage (a);
   c. separating by centrifugation the crystalline citric acid from the concentrated solution coming from (b);
   d. re-cycling the mother liquors of crystallization residual from the separating operation (c) part to the electrodialysis stage (a) and part to the stage of crystallization (b).

2. A process as claimed in claim 1, characterized in that the electrodialysis (a) is carried out at a temperature between 50°C and 90°C.

3. A process as claimed in claim 1, characterized in that the crystallization (b) of the citric acid is carried out at a temperature between 20°C and 60°C.

4. A process as claimed in claim 1, characterized in that the 10% by weight of the mother liquors is recycled to the electrodialysis stage (a) and the remaining 90% to the crystallization stage (b).

5. A process as claimed in claim 1 wherein hot cathodic solution from stage (a) is delivered first into heat exchange relation with the solution of stage (b), then into heat exchange relation with cooling water, and finally to a recovery stage for alkaline hydroxide.

\* \* \* \* \*